United States Patent [19]

Kawata et al.

[11] Patent Number: 4,772,590
[45] Date of Patent: Sep. 20, 1988

[54] OILY COMPOSITION OF ACLARUBICIN OR HYDROCHLORIDE THEREOF

[75] Inventors: Hiroitsu Kawata; Shunji Hasumi; Akira Okada; Masayoshi Aruga, all of Saitama; Toshimitsu Konno, Kumamoto; Ken Iwai, Kumamoto; Hiroshi Maeda, Kumamoto, all of Japan

[73] Assignee: Yamanouchi Pharmaceutical Co., Ltd., Tokyo, Japan

[21] Appl. No.: 880,633

[22] Filed: Jun. 27, 1986

Related U.S. Application Data

[63] Continuation of Ser. No. 627,425, Jul. 3, 1984, abandoned.

[30] Foreign Application Priority Data

Jul. 13, 1983 [JP] Japan .................................. 58-127092

[51] Int. Cl.⁴ .............................................. A61K 31/70
[52] U.S. Cl. ...................................................... 514/34
[58] Field of Search ............................ 514/34; 536/64

[56] References Cited

U.S. PATENT DOCUMENTS 3,988,315 10/1976 Umezawa et al. .................... 536/6.4
4,578,391 3/1986 Kawata et al. ........................ 514/256

OTHER PUBLICATIONS

Aclacinomycin A and Behenoyl Arabinofuranosylcytosine . . . , Sampi, et al., from "Oncology", Reprint vol. 43, No. 1, (pp. 18-22), 1986.
Radiation Biology-Miyamoto, et al., from "Radiology", vol. 149, No. 3, pp. 835-839, Dec. 1983.
Cancer Treatment Reports, vol. 68, No. 6, Jun. 1984-"Phase I-II Study of Aclarubicin for Treatment . . . ", Machover, et al.

Primary Examiner—J. R. Brown
Assistant Examiner—Elli Peselev
Attorney, Agent, or Firm—Burgess, Ryan and Wayne

[57] ABSTRACT

An oily composition of aclarubicin or aclarubicin hydrochloride comprising aclarubicin or aclarubicin hydrochloride; at least one fatty acid selected from saturated medium chain fatty acids, unsaturated medium chain fatty acids and unsaturated long chain fatty acids; and at least one fats and oils selected from iodized oils and vegetable oils.

12 Claims, 1 Drawing Sheet

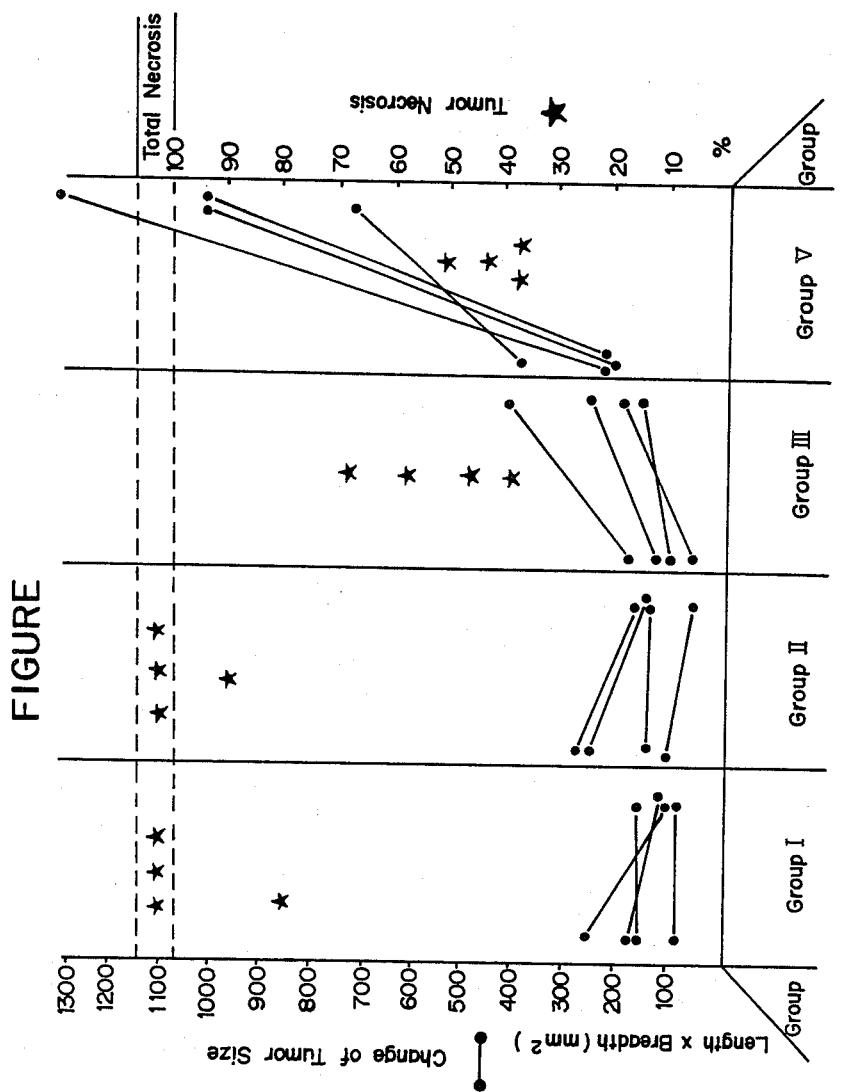
FIGURE

OILY COMPOSITION OF ACLARUBICIN OR HYDROCHLORIDE THEREOF

This application is a continuation, of application Ser. No. 627,425, filed July 3, 1984, now abandoned.

FIELD OF THE INVENTION

This invention relates to an oily composition of aclarubicin or the hydrochloride thereof.

BACKGROUND OF THE INVENTION

An antitumor drug is orally or intravenously administered for treating the special neoplastic tissues. In that case, as the antitumor drug diffuses into the whole body, the concentratration of the antitumor drug in the special neoplastic tissues is lowered, and hence the sufficient treatment effect cannot be obtained as well as undesirable side effects to the living body sometimes occur.

For overcoming these problems, it has been proposed to directly administer a preparation composed of an antitumor drug carried on a carrier having low toxicity such as albumin, synthetic high molecular materials, fats and oils, etc., into a lymph vessel or blood vessels for internal organs.

However, since many important antitumor drugs are water-soluble or sparingly soluble in oils, it is generally difficult to produce preparations of antitumor drugs carried on fats and oils, which are used for the above-described administration method. In fact, as such preparations which are practically used, there is only a preparation of epitiostanol dissolved in sesame oil.

The inventors previously investigated the method of producing the preparations of sparingly oil soluble or water soluble antitumor drugs, which can be used for the above-described administration method and succeeded in producing the preparations of compositions composed of the antitumor drugs, solubilizing adjuvants in oily vehicles such as crown ether, etc., and fats and oils (or an unsaturated higher fatty acid alone) (Japanese Patent Publication (Unexamined) No. 124714/'83).

SUMMARY OF THE INVENTION

However, as the result of various investigations on the production of the above-described compositions of a specific antitumor drug, aclarubicin or aclarubicin hydro-chloride, the inventors have discovered that these antitumor drugs can be dissolved well in specific fatty acids and fats and oils without using the specific solubilizing adjuvants in an oily vehicle such as crown ether, etc., and based on the discovery, the present invention has been accomplished.

That is, according to this invention, there is provided an oily composition of aclarubicin or of aclarubicin hydrochloride comprising aclarubicin or aclarubicin hydro-chloride; at least one fatty acid selected from saturated medium chain fatty acids, unsaturated medium chain fatty acids and unsaturated long chain fatty acids; and at least one fats and oils selected from iodized oils and vegetable oils.

DESCRIPTION OF THE PREFERRED EMBODIMENTS

Aclarubicin is a known antitumor antibiotic of the anthracycline series obtained by the cultivation of Strepto-myces galilaeus or other method and is expressed by the chemical name, methyl(1R, 2R, 4S)-2-ethyl-1,2,3,4,6,11-hexahydro-2,5,7-trihydroxy-6,11-dioxo-4-{[2,3,6-trideoxy-4-O-[2,6-dideoxy-4-O-((2R,6S)-tetrahydro-6-methyl-5-oxo-2H-pyran-2-yl)-α-1-lyxohexopyranocyl]-3-dimethylamino-α-1-lyxo-hexopyranocyl]oxy}-1-naphthacene carboxylate. Usually, the antibiotic is used as aclarubicin hydrochloride.

Aclarubicin hydrochloride is freely soluble in water, acetone, methanol, etc., but is practically insoluble in ether and n-hexane. Aclarubicin hydrochloride is very sparingly soluble in fats and oils. For example, the solubility of aclarubicin hydrochloride in sesame oil is 16 μg/ml and that in olive oil is about 4 μg/ml.

Aclarubicin is sparingly soluble in sesame oil as 10 mg/ml and in olive oil as 10 mg/ml but the composition of this invention can be dissolved in these oils at the solubility about 5 times higher than the solubility of aclarubicin. Accordingly, an antitumor drug solution having a high concentration can be prepared by using the composition of this invention and hence the antitumor drug can reach the special neoplastic tissues at high concentration to increase the treatment effect.

In this invention, saturated or unsaturated medium chain fatty acids or unsaturated long chain fatty acids can be used as fatty acids. The medium chain fatty acids include capric acid, caproic acid, caprylic acid, caproleinic acid, etc., and unsaturated long chain fatty acids include linoleic acid oleic, acid, linolenic acid, etc. These fatty acids may be used solely or as a mixture of them.

Even by using lower fatty acids, the solubilization of aclarubicin or aclarubicin hydro-chloride in fats and oils may be possible but since lower fatty acids have high solubility in water and a large dissociation constant, they cannot be used as they are. On the other hand, saturated long chain fatty acid (e.g., palmitic acid and stearic acid) have very low solubilizing faculty for aclarubicin or aclarubicin hydro-chloride in fats and oils and are in solid states. Therefore, when saturated long chain fatty acids are used in large quantities, the system is solidified, which cannot be used for practical purpose. Also, it has been found that polycarboxylic acids such as fumaric acid, tartaric acid, succinic acid, etc., are not dissolved in fats and oils and hence cannot achieve the solubilization of aclarubicin or aclarubicin hydro-chloride.

That is, only when the fatty acids defined in this invention, the sufficient solubilization of aclarubicin or aclarubicin hydro-chloride in fats and oils can be achieved and the desired oily compositions of these antitumors can be obtained.

As fats and oils in this invention, iodized oils or vegetable oils are used. Iodized oils include iodized poppy seed oil fatty acid ethyl ester (Lipiodol Ultra-Fluide, trade name, made by Laboratoire Guerbert), strong iodized oil (the 9th revised Japanese Pharmacopoeia), iodized oil (the 9th revised Japanese Pharmacopoeia), iodized medium chain or long chain fatty acids, etc., and vegetable oils include sesame oil, peanut oil, cotton seed oil, olive oil, almond oil, etc.

The reason for using these fats and oils in this invention is as follows. That is, when the fats and oils is administered in the artery dominating the tumor portion, the fats and oils are retained at the tumor portion and when, in particular, the iodized oil is used, the diagnosis of the tumor portion becomes possible [Toshimitsu Konno et al "Gan to Kagaku Ryoho (Cancer and Chemotherapy)", 9 (11), 2005–2015(1982) and Kenichiro Nakakuma et al, "Nichidoku Iho" (Japan and Germany Medical Report):, 24(4), 675–682(1979)]. Among these fats and oils, iodized poppy seed oil fatty acid ethyl ester is particularly preferred.

The compounding ratio of the fatty acid in the composition of this invention is 10–1,000 parts by weight (preferably 30–200 parts by weight) per 1 part by weight of aclarubicin hydro-chloride and 1–1,000 parts by weight (preferably 1–50 parts by weight) per 1 part by weight of aclarubicin.

Furthermore, the composition of this invention may further contain, if desired, an antioxidant (α-tocopherol, etc.,) and other additives.

The composition of this invention can be prepared by mixing aclarubicin or aclarubicin hydro-chloride with at least one of the above-described fatty acids and at least one of the above-described fats and oils. In this case, when dissolving the components is insufficient, shaking or stirring may be employed for certainly performing the dissolving. In particular, when a vegetable oil is used, the dissolving is completely performed by using a stirring mixer, an ultrasonic wave bath, etc.

Also, the composition of this invention may be a preparation of the type that is converted into a solution at use. That is, in the case of using aclarubicin hydro-chloride, it is dissolved in water and the solution is lyophilized in a proper vessel (for example, vials). In the case of using aclarubicin, it is dissolved in a proper organic solvent such as 1,4-dioxane and the solution is lyophilized in a proper vessel. Apart from this, at least one of the above-described fatty acids and at least one of the above-described fats and oils are mixed and the liquid is placed in a proper container such as an ampoule. At use, the liquid was added to the above-described lyophilized antitumor and the antitumor is dissolved in the liquid to provide the liquid composition of this invention.

The proper concentration of aclarubicin hydro-chloride or aclarubicin in the composition of this invention is 1 mg(potency)/1 ml to 100 mg(potency)/1 ml.

Then, for proving the usefulness of the composition of this invention, the antitumor effect of the composition for rabbits is explained hereinafter together with the experimental procedure.

Experimental procedure:

Using New Zealand White rabbits, the abdomen of each rabbit was opened under the anesthesia with Pentobarbital and 0.1 ml of a suspension containing 1,000,000 to 1,500,000 VX2 cancer cells in 1 ml of the suspension was injected to subserosal tissue of the left lateral lobe of the liver of each rabbit. After 2 weeks following the injection, it was confirmed that the tumor size became 1 to 2 cm and then the rabbits were subjected to the following experiment.

Group I: Aclarubicin hydro-chloride oily solution-administered group (4 rabbits).

That is, 0.2 ml of the aclarubicin hydro-chloride oily solution (12.5 mg/ml) obtained in Example 12 shown below was injected into the common hepatic artery of each rabbit under the laparotomy.

The following experiments were also performed by the same administration method as above.

Group II: Aclarubicin oily solution-administered group (4 rabbits).

In the experiment, 0.2 ml of the aclarubicin oily solution (25 mg/ml) obtained in Example 13 shown below was injected into each rabbit by the same manner as above.

Group III: Group simultaneously administered with aqueous aclarubicin hydro-chloride solution and Lipiodol Ultra-Fluide (4 rabbits).

In the experiment, 0.25 ml of aqueous aclarubicin hydro-chloride solution (20 mg/ml) was injected into each rabbit and immediately thereafter 0.2 ml of Lipiodol Ultra-Fluide was injected into the rabbit.

Group IV: Aqueous acularubicin hydro-chloride solution-administered group (3 rabbits):

In the experiment, 2.5 ml of an aqueous aclarubicin hydro-chloride solution (20 mg/ml) was injected into each rabbit.

Group V: Lipiodol Ultra-Fluide alone-administered group (4 rabbits).

In the experiment, 0.2 ml of Lipiodol Ultra-Fluide was injected into each rabbit.

After a week since the injection of samples, the rabbits were sacrificed and then the Softex radiographs and the histological analysis were performed.

Experimental result:

The change ( —● ) of the tumor size and the ratio ( ★ ) of the tumor necrosis at the sacrifice of the rabbits from group I to group V are shown in the FIG.

In the case of using Lipiodol Ultra-Fluide alone, the necrosis caused by the embolization of the new blood vessel was confirmed a little but the total necrosis was not obtained and the tumor size increased. On the other hand, in the aclarubicin hydro-chloride oily solution-administered group and the aclarubicin oily solution-administered group, the increase of tumor size was not observed, the total nercosis was observed in 3/4 of the rabbits, that is the tumor portions changed into light grey and were softened, which showed that the tumor portions were mostly in the degenerative and necrotic states in pathological tissues. At the periphery of the tumor, the remarkable inflammatory cell infiltration, in particular the lymphocytic infiltration, was observed.

On the other hand, in Group III simultaneously administered with an aqueous aclarubicin hydro-chloride solution and Lipiodol Ultra-Fluide, the necrosis was observed a little, but the result was almost same as the case of using Lipiodol Ultra-Fluide alone and viable cancer cells were observed in both cases. From the X-ray photographs, in Group I, Group II, Group III and Group V, Lipiodol Ultra-Fluide was observed at the tumor portions alone in each case. Also, in Group IV wherein an aqueous aclarubicin hydro-chloride solution was administered in an amount of 20 times (as aclarubicin) that of the oily solution of aclarubicin, a necrosis phase was observed at the center of the tumor portion but viable cancer cells were observed in each case.

From the above experimental results, it is clear that the composition of this invention wherein aclarubicin hydro-chloride or aclarubicin is solubilized in Lipiodol Ultra-Fluide shows the remarkable antitumor effect as compared with the case of administering Lipiodol Ultra-Fluide alone, the case of administering an aqueous aclarubicin hydro-chloride solution of 20 times (as aclarubicin hydro-chloride) that of the oily solution, and the case of simultaneously administering an aqueous aclarubicin hydro-chloride solution and Lipiodol Ultra-Fluide.

Then, the invention will be further explained by the following examples.

EXAMPLE 1

To 1 g (potency) of aclarubicin hydro-chloride were added 22.6 g of linoleic acid and 96.2 g of an iodized poppy seed oil fatty acid ethylester (Lipiodol Ultra-Fluid, trade name) and the mixture was shaken to provide a transparent solution.

EXAMPLE 2

To 20 mg (potency) of aclarubicin hydro-chloride were added 0.5 ml of oleic acid and 1.5 ml of the iodized poppy seed oil fatty acid ethylester (same as in Example 1) and the mixture was shaken to provide a transparent solution.

EXAMPLE 3

To 30 mg (potency) of aclarubicin hydro-chloride were added 500 mg of n-capric acid and 1.5 ml of the iodized poppy seed oil fatty acid ethylester and the mixture was shaken to provide a transparent solution.

EXAMPLE 4

To 100 mg (potency) of aclarubicin hydro-chloride were added 1.8 g of linoleic acid, 200 mg of egg lecithin, 50 mg of α-tocopherol, and 7.9 g of the iodized poppy seed oil fatty acid ethylester (as in Example 1) and the mixture was shaken to provide a transparent solution.

EXAMPLE 5

To 50 mg (potency) of aclarubicin were added 0.5 ml of linoleic acid and 1.5 ml of the iodized poppy seed oil fatty acid ethylester (as in Example 1) and the mixture was shaken to provide a transparent solution.

EXAMPLE 6

To 50 mg (potency) of aclarubicin were added 100 mg of n-capric acid and 1 ml of the iodized poppy seed oil fatty acid ethylester (as in Example 1) and the mixture was shaken to provide a transparent solution.

EXAMPLE 7

In 1,4-dioxane was dissolved 50 mg (potency) of aclarubicin and the solution was lyophilized. To the lyophilized product was added a mixture of 0.18 g of linolic acid and 2.31 g of the iodized poppy seed oil fatty acid ethylester (as in Example 1), whereby aclarubicin was quickly dissolved to provide a transparent solution.

EXAMPLE 8

To 50 mg (potency) of aclarubicin were added 50 mg of α-tocopherol and further 0.5 ml of oleic acid and 1.5 ml of the iodized poppy seed oil fatty acid ethylester (as in Example 1), and the mixture was shaken to provide a transparent solution.

EXAMPLE 9

To 53 mg (potency) of aclarubicin were added 0.5 ml of linoleic acid and 1 ml of sesame oil and the mixture was immersed in an ultra sonicator bath at 80 watts for 10 minutes to provide a transparent solution.

EXAMPLE 10

To 50 mg (potency) of aclarubicin were added 0.2 ml of oleic acid and further 1 ml of peanut oil and the mixture was shaken to provide a transparent solution.

EXAMPLE 11

To 25 mg (potency) of aclarubicin hydro-chloride were added 0.5 ml of linoleic acid and 0.2 ml of sesame oil and the mixture was immersed in an ultra sonicator bath at 80 watts for 10 minutes to provide a transparent solution.

EXAMPLE 12

To 2 g (potency) of aclarubicin hydro-chloride were added 72 g of linoleic acid and 103 g of the iodized poppy seed oil fatty acid ethylester and the mixture was shaken vigorously to provide a transparent solution.

EXAMPLE 13

To 3.0 g (potency) of aclarubicin were added 22 g of linoleic acid and 120 g of the iodized poppy seed oil fatty acid ethylester and the mixture was shaken vigorously by means of a shaker to provide a transparent solution.

The solutions obtained in the above-described examples are used as injections.

What is claimed is:

1. An oily composition of aclarubicin or aclarubicin hydrochloride said composition consisting of aclarubicin or aclarubicin hydrochloride; at least one fatty aicd selected from saturated medium chain fatty acids, unsaturated medium chain fatty acids and unsaturated long chain fatty acids; wherein the compounding ratio of the fatty acid is about 32 to 200 parts by weight per 1 part by weight of aclarubicin hydrochloride or about 1 to 50 parts by weight per part by weight of aclarubicin; and at least one fat and oil selected from iodized oils and vegetable oils.

2. An oily composition of aclarubicin consisting of aclarubicin, at least one fatty acid selected from saturated medium chain fatty acids, unsaturated medium chain fatty acids and unsaturated long chain fatty acids; wherein the compounding ratio of the fatty acid is about 1 to 50 parts by weight per part by weight of aclarubicin; and at least one fat and oil selected from iodized oils and vegetable oils.

3. An oily composition of aclarubicin hydrochloride, said composition consisting of aclarubicin hydrochloride, at least one fatty acid selected from saturatead medium chain fatty acids, unsatuarated medium chain fatty acids and unsaturated long chain fatty acids; wherein the compounding ratio of the fatty acid is about 32 to 200 parts by weight per 1 part by weight of aclarubicin hydrochloride; and at least one fat and oil selected from iodized oils and vegetable oils.

4. The oily composition as claimed in claim 1, wherein the concentration of aclarubicin or aclarubicin hydrochloride is 1 mg (potency) to 100 mg (potency) per 1 ml of the composition.

5. The oily composition as claimed in claim 1, wherein said fatty acid is linoleic acid.

6. The oily composition as claimed in claim 1, wherein said fatty acid is oleic acid.

7. The oily composition as claimed in claim 1, wherein said fatty acid is capric acid.

8. The oily composition as claimed in claim 1, wherein said fatty acid is linolenic acid.

9. The oily composition as claimed in claim 1, wherein said oil is iodized poppy seed oil fatty acid ethylester.

10. The oily composition as claimed in claim 1, wherein said oil is sesame oil.

11. The oily composition as claimed in claim 1, wherein said oil is soy bean oil.

12. The oily composition as claimed in claim 1, wherein said oil is cotton seed oil.

* * * * *